United States Patent
Soon-Shiong

(10) Patent No.: US 12,194,111 B2
(45) Date of Patent: Jan. 14, 2025

(54) ALPHA EMITTER COMPOSITIONS AND METHODS

(71) Applicant: Nant Holdings IP, LLC, Culver City, CA (US)

(72) Inventor: Patrick Soon-Shiong, Culver City, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 354 days.

(21) Appl. No.: 17/275,978

(22) PCT Filed: Sep. 13, 2019

(86) PCT No.: PCT/US2019/051111
§ 371 (c)(1),
(2) Date: Mar. 12, 2021

(87) PCT Pub. No.: WO2020/081174
PCT Pub. Date: Apr. 23, 2020

(65) Prior Publication Data
US 2022/0040338 A1    Feb. 10, 2022

Related U.S. Application Data

(60) Provisional application No. 62/746,496, filed on Oct. 16, 2018.

(51) Int. Cl.
*A61K 51/08* (2006.01)
*A61K 51/04* (2006.01)
*A61K 51/10* (2006.01)

(52) U.S. Cl.
CPC ........ *A61K 51/081* (2013.01); *A61K 51/0478* (2013.01); *A61K 51/048* (2013.01); *A61K 51/0482* (2013.01); *A61K 51/10* (2013.01)

(58) Field of Classification Search
CPC .............. A61K 51/0482; A61K 51/088; A61K 51/10; A61K 51/0478; A61K 51/081; A61K 51/1096; A61K 51/1093; A61K 51/048; A61P 35/00
See application file for complete search history.

(56) References Cited

U.S. PATENT DOCUMENTS

| | | | |
|---|---|---|---|
| 4,618,492 | A | 10/1986 | Blattler et al. |
| 4,988,496 | A | 1/1991 | Srinivasan et al. |
| 5,306,809 | A | 4/1994 | Boon et al. |
| 7,902,144 | B2 | 3/2011 | Kratz |
| 8,846,602 | B2 | 9/2014 | Kratz |
| 2005/0186214 | A1 | 8/2005 | Liu et al. |
| 2011/0053878 | A1 | 3/2011 | Yang et al. |
| 2016/0089388 | A1 | 3/2016 | Levitt |
| 2017/0258936 | A1 | 9/2017 | Berkman et al. |
| 2017/0354744 | A1 | 12/2017 | Evans et al. |

FOREIGN PATENT DOCUMENTS

| | | | |
|---|---|---|---|
| WO | 2011/098611 A2 | 8/2011 | |
| WO | 2013/124068 A1 | 8/2013 | |
| WO | 2014/093815 A1 | 6/2014 | |
| WO | 2016/028700 A1 | 2/2016 | |
| WO | WO-2016046793 A2 * | 3/2016 | ......... A61K 51/0474 |
| WO | 2020/081174 A1 | 4/2020 | |

OTHER PUBLICATIONS

Antezek et al., Bioconjugate Chem. 2006, 17, p. 1551-1560. (Year: 2006).*
Kratz et al., Invest New Drugs, 2012, 30, p. 1743-1749. (Year: 2012).*
Scheinberg et al., Curr Radiopharm., 2011, 4(4), p. 306-320. (Year: 2011).*
International Search Report and Written Opinion receieved for PCT Application Serial No. PCT/US2019/051111 dated Jan. 2, 2020, 11 pages.
Liu Shuang, "Bifunctional coupling agents for radiolabeling of biomolecules and target-specific delivery of metallic radionuclides", Advanced Drug Delivery Reviews, 2008, vol. 60, pp. 1347-1370.
Hoogenboezem et al., "Harnessing albumin as a carrier for cancer therapies", Advanced Drug Delivery Reviews, 2018, vol. 130, pp. 73-89.
Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemical, 1998, vol. 9, pp. 72-86.
Tsuchikama et al., "Antibody-drug conjugates: recent advances in conjugation and linker chemistries", Protein Cell, 2018, vol. 9, No. 1, pp. 33-46 (Cited from Specification).
Dekempeneer et al., "Targeted alpha therapy using short-lived alpha-particles and the promise of nanobodies as targeting vehicle", Expert Opinion on Biological Theraphy, 2016, vol. 16, No. 8, pp. 1035-1047 (Cited from Specification).
Kratz et al., "Drug-polymer conjugates containing acid-cleavable bonds", Critical Reviews in Therapeutic Drug Carrier Systems, 1999, vol. 16, No. 3, 2 pages (Cited from Specification).
Gatenby et al., "Acid-Mediated Tumor Invasion: a Multidisciplinary Study", Cancer Research, 2006, vol. 66, No. 10, 5216-5223 (Cited from Specification).
Rafati et al., "Protein-loaded poly(dl-lactide-co-glycolide) microparticles for oral administration: formulation, structural and release characteristics", Journal of Controlled Release, vol. 43, No. 1, 1997, pp. 89-102 (Cited from Specification).
Quirk et al., "Stimulation of medial prefrontal cortex decreases the responsiveness of central amygdala output neurons", The Journal of Neuroscience, 2003, vol. 23, No. 25, pp. 8800-8807 (Cited from Specification).
Yabbaorv et al., "A new system for targeted delivery of doxorubicin into tumor cells" Journal of Controlled Release, Jun. 10, 2013, vol. 168, No. 2, 19 pages.

(Continued)

*Primary Examiner* — Michael G. Hartley
*Assistant Examiner* — Leah H Schlientz
(74) *Attorney, Agent, or Firm* — Martin Fessenmaier; Umberg Zipser LLP

(57) ABSTRACT

Compositions, methods, and uses of an alpha emitter are provided in which the alpha emitter is coupled to carrier protein via a cleavable coupling moiety. The coupling moiety is preferably cleavable in an acidic tumor microenvironment, and as such will enrich the alpha emitter upon cleavage within the tumor microenvironment.

7 Claims, 2 Drawing Sheets

(56) References Cited

OTHER PUBLICATIONS

Scheinberg et al., "Actinium-225 in targeted alpha-particle therapeutic applications", Curr Radiopharm., Oct. 2011, vol. 4, No. 4, pp. 306-320.
Vaidyanathan et al., "Astatine Radiopharmaceuticals: Prospects and Problems", Curr Radiopharm., Sep. 1, 2008, vol. 1, No. 3, 42 page.
Lowry et al., "Oral Chelation Therapy for Patients with Lead Poisoning" Division of Clinical Pharmacology and Medical Toxicology, The Children's Mercy Hospitals and Clinics, Dec. 2010, p. 1-33.
International Preliminary Report on Patentability Chapter I received for PCT Application Serial No. PCT/US2019/051111 dated Apr. 29, 2021, 9 pages.

\* cited by examiner

| Isotope | Daughter isotopes* | Physical half-life | Maximum energy (keV) | Occurrence (%) | Associated emissions |
|---|---|---|---|---|---|
| $^{211}$At | – | 7.2 h | 5.867 | α (41.8%) | α, γ, LEE |
| | $^{211}$Po | 516 ms | 7.450 | α (100%) | |
| $^{225}$Ac | – | 10 days | 5.830 | α (100%) | α, γ, Auger, β⁻ |
| | $^{221}$Fr | 4.9 min | 6.341 | α (100%) | |
| | $^{217}$At | 32.3 ms | 7.069 | α (99.98%)/β⁻ (0.01%) | |
| | $^{213}$Bi | 45.6 min | 6.051 | α (2.2%)/ β⁻(97.8%) | |
| | $^{213}$Po | 4.2 μs | 8.377 | α (100%) | |
| $^{213}$Bi | – | 45.6 min | 6.051 | α (2.2%)/β⁻ (97.8%) | α, γ, Auger, β⁻ |
| | $^{213}$Po | 4.2 μs | 8.377 | α (100%) | |
| $^{212}$Bi | – | 61 min | 5.870 | α (36%)/β⁻ (64%) | α, γ, Auger, β⁻ |
| | $^{212}$Po | 298 ns | 8.785 | α (100%) | |
| $^{227}$Th | – | 18.72 days | 6.038 | α (100%) | α, γ, Auger, β⁻ |
| | $^{223}$Ra | 11.4 days | 5.871 | α (100%) | |
| | $^{219}$Rn | 4 s | 6.819 | α (100%) | |
| | $^{215}$Po | 1.8 ms | 7.386 | α (100%) | |
| | $^{211}$Bi | 2.14 min | 6.623 | α (99.7%)/β⁻ (0.3%) | |
| $^{212}$Pb | – | 10.64 h | | β⁻ (100%) | β⁻ |
| | $^{212}$Bi | 61 min | 5.870 | α (36%)/β⁻ (64%) | α, γ, Auger, β⁻ |
| | $^{212}$Po | 0.3 μs | 8.785 | α (100%) | |
| $^{223}$Ra | – | 11.4 days | 5.871 | α (100%) | α, γ, Auger, β⁻ |
| | $^{219}$Rn | 4 s | 6.819 | α (100%) | |
| | $^{215}$Po | 1.8 ms | 7.386 | α (100%) | |
| | $^{211}$Bi | 2.14 min | 6.623 | α (99.7%)/β⁻ (0.3%) | |

*Generated α-particle emitter after decay of the conjugated parent.
LEE: Low-energy electron emission; NS: yield not significant.

Fig.1

|  | Strategy | DAR[a] | Advantages | Disadvantages |
|---|---|---|---|---|
| Chemical conjugation | Lysine coupling | 0-7 | Simple process<br>Used in FDA-approved and clinically tested ADCs | Distributed DAR<br>Heterogeneous mixtures of products<br>Potential reduction of antigen binding |
|  | Cysteine coupling | 0, 2, 4, 6, 8 | Simple process<br>Used in FDA-approved and clinically tested ADCs | Heterogeneous mixtures of products<br>Increased clearance rate with high DAR |
|  | THIOMAB | 2 | Defined DAR<br>Homogeneity | Requires genetic engineering |
|  | Cysteine rebridging | 4 | Defined DAR<br>Homogeneity<br>High structural stability | Potential disulfide scrambling |
|  | Non-natural amino acid | 2 | Defined DAR<br>Homogeneity | Requires special techniques and biological agents<br>Potential immunogenicity |
|  | Sortase | 3-4 | Tightly-controlled DAR<br>No adverse effect on antibody binding | Requires incorporation of LPETG motif on the heavy chain |
| (Chemo)enzymatic conjugation | Microbial transglutaminase | 2 | Defined DARs<br>Homogeneity | Requires removal of N-glycan on N297 |
|  | Glycan engineering (GlycoConnect) | 2 | Defined DARs<br>Homogeneity | Requires multiple steps (i.e., N-glycan trimming, glycosylation, and conjugation) |
| Cleavable Linker | Hydrazone |  | pH-responsive cleavage | Premature cleavage during circulation |
|  | Val-Cit[b]-PABC[c], Val-Ala-PABC[c] |  | Stability during circulation<br>Traceless release of payload | Hydrophobicity |
|  | Disulfide |  | Intracellular release of payload | Potential premature cleavage during circulation |
|  | Pyrophosphate diester |  | Stability during circulation<br>Hydrophilicity<br>Traceless release of payload | Unknown mechanism of lysosomal cleavage |
| Non-cleavable Linker | Stable linker without cleavage mechanism |  | Stability during circulation | An amino acid residue attached on the released payload |

[a] DAR, Drug-to-antibody ratio; [b] Cit, citrulline; [c] PABC, p-aminobenzyloxycarbonyl.

Fig.2

ALPHA EMITTER COMPOSITIONS AND METHODS

This application claims priority to our U.S. provisional patent application with the Ser. No. 62/746,496, which was filed Oct. 16, 2018, and is incorporated by reference herein.

FIELD OF THE INVENTION

The field of the invention is compositions and methods for radiotherapy, especially as it relates to target selective delivery of alpha emitters to a tumor tissue.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The tumor microenvironment is a cellular environment that is created by tumor cells and maintained by tumor cell and other non-tumor cells including various immune cells, fibroblasts, and extracellular matrix. It is generally hypothesized that initial rapid growth of tumor cells in the tumor often creates disparity between the oxygen supply through vascularization and oxygen demand of growing cells, which results in hypoxic condition in the tumor microenvironment. In addition, hypoxic conditions also cause accumulation of acidic metabolites (e.g., from anaerobic glycolysis) in the extracellular microenvironment. Unfortunately, the so created hypoxic and acidic tumor microenvironment provides a protective mechanism for a tumor against an immune response and immune therapy. Moreover, the acidic tumor microenvironment also favors the accumulation of myeloid derived suppressor cells (MDSC) and/or induction of endothelial-mesenchymal transition (EMT) of the tumor cells.

In an effort to target tumor cells in a manner that is independent of the microenvironment in the tumor, antibodies can be conjugated with a variety of effector molecules (e.g., cytostatic or toxic drugs, labeling agents, etc.) to form an antibody-drug conjugate (ADC; see e.g., *Protein Cell* 2018, 9(1):33-46). Such ADC will effectively bind selected epitopes on a tumor cell and so deliver a therapeutic payload. Alternatively, alpha emitters have been coupled to antibodies to so deliver localized therapy to a tissue that is targeted by the antibody (see e.g., *Expert Opin Biol Ther.* 2016 Aug. 2; 16(8): 1035-1047). However, such approach is generally dependent on target specificity and is typically not suitable where a tumor specific epitope is not readily available.

In an alternative approach, doxorubicin was modified with maleimidocaproyl hydrazone to so form a reagent that covalently couples to albumin. Advantageously, albumin acts as carrier protein for nutrients and is readily taken up into the tumor microenvironment. Moreover, as the hydrazone linker is instable at acidic pH, doxorubicin is cleaved from albumin and is specifically delivered to the tumor. Unfortunately, a clinical trial with modified doxorubicin (aldoxorubicin) as a cytotoxic agents did not show a significant increase in progression free disease for treatment of relapsed or refractory soft tissue sarcoma. In yet another effort using albumin as a delivery vehicle, nanoparticle albumin-bound paclitaxel (abraxane) is administered and preferentially accumulates in breast cancer tumor tissues. While notably effective in at least some cases, the preparation of abraxane is not trivial, and the cost for abraxane compared to paclitaxel alone is substantially higher. Still further, paclitaxel and abraxane are only indicated for a limited number of cancers.

Therefore, even though various drug conjugates are known in the art, various difficulties nevertheless remain. Consequently, there is still a need for improved compositions, methods for and uses for targeted drug conjugates.

SUMMARY OF THE INVENTION

The inventive subject matter is directed to various compositions and methods of alpha emitters that are coupled to carrier protein via a cleavable coupling moiety. The coupling moiety is preferably cleavable in an acidic tumor microenvironment, and will enrich the alpha emitter upon cleavage within an acidic tumor microenvironment.

In one aspect of the inventive subject matter, the inventor contemplates synthetic alpha-emitter-conjugated compound that comprises an alpha-emitter that is coupled to a coupling moiety with a linker portion and a chelator portion. The linker portion has a protein binding group and the chelator portion chelates the alpha-emitter, while the coupling moiety is preferentially cleavable in a tumor microenvironment.

Preferably, suitable alpha-emitters include $^{225}$Ac, $^{211}$At, $^{212}$Pb and $^{213}$Bi, or $^{223}$Ra, and contemplated chelator portion comprise multidentate chelators and macrocyclic chelators. For example, suitable chelator portion may comprise diethylenetriaminepenta acetic acid (DTPA), 1,4,8,11-tetraazacyclotetradecane-1,4,8,11-tetraacetic acid (TETA), DOTA, 1,4,7,10-tetraazacyclododecane-1,4,7,10-tetrapropionic acid (DOTPA), 1,4,8,11-tetraazacyclo tetradecane-1,4,8,11-tetrapropionic acid (TETPA), or 1,4,7,10-tetraazacyclododecane-1,4,7,10-tetramethylenephosphonic acid (DOTMP), diethylenetriamine pentaacetic acid (DTPA), a calix[4] arene, meso-2,3 dimercapto succinic acid (DMSA, Succimer), etheylene diamine tetraacetic acid (EDTA), racemic-2,3-dimercapto-1-propanesulfonic acid (DMPS, Unithiol), penicillamine, desferrioxamine, deferiprone, ethylenediaminetetraacetic (EDTA), diethylenetrinitrilopentaacetic acid (DTPA), and nitrilotris(methylene)triphosphonic acid (NTTA).

In further contemplated embodiments, the protein binding group may be a thiol reactive group, a hydroxyl reactive group, or an amino reactive group (e.g., a thiol group, a maleimide group, or an acid chloride group), while the coupling moiety may comprise an acid-labile portion, a photo-cleavable portion, and a portion cleavable by an enzyme. Therefore, among other options, the coupling moiety comprises a hydrazone group. Moreover, it is contemplated that a protein may be coupled to the protein binding group (e.g., an antibody or a fragment thereof, or albumin or other serum protein).

Viewed from a different perspective, the inventors also contemplate a pharmaceutical composition that comprises the compounds contemplated herein, typically formulated for injection. For example, such compositions will have a radioactivity of between 0.1 and 10 mBq/dosage unit. Therefore, the inventor also contemplates a method of treating a tumor that includes a step of administering a pharmaceutical composition as presented herein to a patient in need thereof. Similarly, uses of alpha-emitter-conjugated compound in the treatment of a tumor are contemplated.

Viewed from yet another perspective, the inventor also contemplates a method of preferentially delivering an alpha-emitter to a tumor that includes a step of administering an alpha-emitter that is coupled to a coupling moiety that has a linker portion and a chelator portion, wherein the linker portion has a protein binding group and wherein the chelator portion chelates the alpha-emitter, and wherein the coupling moiety is preferentially cleavable in a tumor microenvironment. With respect to suitable compounds, the same considerations as noted above apply.

Various objects, features, aspects and advantages of the inventive subject matter will become more apparent from the following detailed description of preferred embodiments.

BRIEF DESCRIPTION OF THE DRAWING

FIG. 1 shows a table of exemplary contemplated alpha emitters and associated properties.

FIG. 2 shows a table of exemplary protein binding groups.

DETAILED DESCRIPTION

Targeted alpha therapy has recently gained attention with the FDA approval of $^{223}$Ra in the treatment of metastatic castration resistant prostate cancer, and various additional drugs using alpha emitters are currently in development, typically coupling the alpha emitter to an antibody. With a charge of +2, α-particles are effective ionization agents with a high linear energy transfer (typically 50-230 keV/μm) at a range of 50-100 μm in tissue. Alpha particles induce clusters of DNA damage such as double-stranded DNA breaks and base chemical modifications that trigger a large number of cellular responses and pathways that include apoptosis, autophagy, necrosis, and cell-cycle arrest. Moreover, alpha radiation damage is independent from the generation of indirect ROS, leaving their effectiveness potentially unabated by tumor hypoxia. However, the availability of suitable antibodies, and technical challenges of labelling the antibody with the alpha emitter are significant.

The inventor has now discovered that targeted alpha therapy compositions can be readily prepared by chelating an alpha emitter to a coupling moiety that has a chelator portion and a linker portion. Advantageously, the linker is cleavable under certain environmental conditions in the tumor microenvironment (e.g., as a function of pH, presence of enzymes, etc.) to so enrich or increase the concentration of the alpha emitter in the tumor microenvironment. For example, a compound according to the inventive subject matter will have the structure A*-C in which A* is the alpha emitter, in which C is a coupling moiety. Most preferably, the coupling moiety will have a chelator portion that binds the alpha emitter and a linker portion that has a reactive group suitable for covalent coupling of the group with a pendant (e.g., SH or OH or NH$_2$) or terminal group (e.g., COOH or NH$_2$) of a polypeptide chain. In further preferred aspects, the chelator can be a multidentate chelator or macrocyclic chelator, and/or the linker portion will allow for (a) covalent coupling of the linker to a protein and (b) hydrolysis of the chelator from the linker portion.

For example, the chelator portion may be functionalized with a hydrazine group (e.g., alkylhydrazine or arylhydrazine group) that is then reacted with a carbonyl group of the linker portion, or the linker portion may be functionalized with a hydrazine group (e.g., alkylhydrazine or arylhydrazine group) that is then reacted with a carbonyl group of the chelator portion. In the reaction product, the linker portion and the chelator portion are thus covalently coupled to each other via an acid labile hydrazone group. An exemplary molecule is depicted in Formula I below.

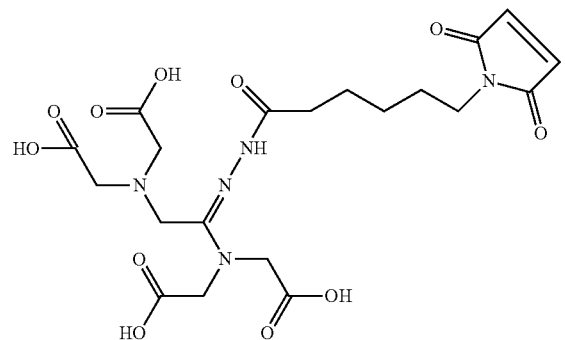

Formula I

As will be readily appreciated, the (EDTA) chelator portion in in such compounds will be cleavable from the (6-caproylmaleimidio) linker portion under acidic conditions present in the tumor microenvironment, while the maleimide group of the linker portion will readily react with thiol groups of various proteins (e.g., C34 of albumin). As such, where the chelator portion will chelate an alpha emitter and where the linker portion binds to albumin, the alpha emitter can be effectively enriched in the tumor microenvironment, typically via gp60 transcytosis in the tumor neovasculature. Advantageously, where the tumor microenvironment is acidic, the chelator will be hydrolytically cleaved from the linker/albumin and remain in the tumor microenvironment along with the alpha emitter.

Of course it should be recognized that the coupling moiety need not be limited to the chelator and linker as exemplarily depicted above, that the chelator will vary depending on the particular alpha emitter chosen, and that the linker may be selected depending on the particular carrier or targeting protein. Thus, carrier/targeting proteins other than albumin are also expressly contemplated herein.

As will be readily appreciated, suitable alpha emitters are used in elemental or ionic form and will in most cases be a metal or metalorganic compound. Therefore, in preferred aspects of the inventive subject matter, the alpha emitter will be a radioactive element, and particularly may be $^{223}$Ra, $^{225}$Ac, $^{211}$At, $^{212}$Pb, or $^{213}$Bi. Advantageously, such radionuclides can be readily bound to a chelator in a specific and tight manner (e.g., $K_D<10^{-6}$M), wherein the chelator may then be further bound to a linker portion. Alternatively, the radioactive element may also be covalently bound to an organic molecule to form an organometallic compound. For example, organobismth compounds can be prepared by reaction of organolithium compound with BiCl$_3$, while various organolead compounds can be synthesized from desirable Grignard reagents and lead chloride. Similarly, contemplated actinium compounds include actinium polyphosphonate compounds. Moreover, it should be noted that while alpha emitters are typically preferred (due to relatively low linear energy transfer), beta emitters are also deemed suitable for use herein. FIG. 1 exemplarily lists suitable alpha emitters and associated properties. For example, contemplated beta emitters include $^{33}P$, $^{32}P$, $^{89}Sr$, $^{67}Cu$, and $^{90}Y$, which may be prepared and/or delivered as organophosphates or as chelates as further described herein.

However, and only for simplicity of preparation, it is preferred that radioactive elements contemplated herein will be bound by a chelator that is present in a chelator portion. Suitably, such chelator portions may comprise multidentate chelators and macrocyclic chelators. For example, suitable chelator portions may comprise diethylenetriaminepenta acetic acid (DTPA), 1,4,8,11-tetraazacyclotetradecane-1,4,8,11-tetraacetic acid (TETA), DOTA, 1,4,7,10-tetraazacyclododecane-1,4,7,10-tetrapropionic acid (DOTPA), 1,4,8,11-tetraazacyclo tetradecane-1,4,8,11-tetrapropionic acid (TETPA), or 1,4,7,10-tetraazacyclododecane-1,4,7,10-tetramethylenephosphonic acid (DOTMP), diethylenetriamine pentaacetic acid (DTPA), a calix[4]arene, meso-2,3 dimercapto succinic acid (DMSA, Succimer), etheylene diamine tetraacetic acid (EDTA), racemic-2,3-dimercapto-1-propanesulfonic acid (DMPS, Unithiol), penicillamine, desferrioxamine, deferiprone, ethylenediaminetetraacetic (EDTA), diethylenetrinitrilopentaacetic acid (DTPA), and nitrilotris(methylene)triphosphonic acid (NTTA).

As will be readily appreciated, the appropriate choice of chelators will depend on the particular radionuclide and further desired modification that connects the chelator portion to the linker portion. Indeed, it is contemplated that all combinations of radionuclide and chelators are deemed suitable for use herein to so immobilize a radionuclide to a chelator or other carrier. In still further contemplated aspects, the chelator portion will also be (covalently) coupled to a linker portion, wherein the (covalent) coupling may advantageously include a cleavable or hydrolysable element that can be preferentially or selectively cleaved or hydrolyzed in the tumor microenvironment.

Preferred linker portions will typically have sufficient stability in blood or plasma to allow circulation while the linker portion is coupled to the chelator portion to so localize to the tumor (microenvironment) without premature cleavage. However, the coupling of the linker portion to the chelator portion must also possess the ability to be rapidly cleaved to release the chelator and alpha emitter when reaching the tumor (microenvironment). Moreover, while not as important, it is generally preferred that the coupling moiety will avoid hydrophobicity that would result in an aggregation of the coupling moieties. In some aspects of the inventive subject matter, the coupling of the linker portion to the chelator portion is cleavable, for example, by low pH conditions, by an enzyme, by a photolabile group, or by a radiolabile group.

For example, linker groups that are selectively hydrolyzed or decomposed at acidic pH have received considerable attention because the majority of receptor-directed drugs are delivered to endosomal compartments or lysosomes where pH values are thought to be low (*Crit Rev Ther Drug Carrier Syst* 16, 245-288 (1999)). The slightly acidic microenvironment of some tumors (~pH 6.5) has also been shown to assist in release of these drugs, especially when the conjugate is expected to be trapped within the tumor for prolonged periods (*Cancer Res* 66: 5216-5223 (2006)).

Several acid labile linkers have been reported for conjugations of certain classes of small molecules, cytotoxic agents and antibodies. In-depth description of these linkers can be found in US 2011/0053878A1 and PCT/EP2013/000513. Several other publications also describe such linkers (e.g., *Journal of Controlled Release* 73: 89-102 (2002); and *Cancer Research Journal* 50: 8800-8807 (1997)). Still further contemplated pH sensitive linkers are linkers that have tunable cleavability as described in US2017/0258936, incorporated by reference herein. For example, tunable cleavable linkers include a phosphoramidate linker scaffold that is tunable by altering the distance, orientation, and flexibility of the neighboring ionizable moiety to the phosphorus core. Increasing this distance will result in both increased acid and physiological stability thus enabling predictable and tunable rate of drug or chelator portion release. Therefore, suitable acid-cleavable moieties include acetal groups, ketal groups, imine groups, hydrazone groups, carboxylhydrazone groups or sulphonylhydrazone groups, or cis-aconityl groups.

In other examples, the cleavable moiety is enzyme-cleavable. Among other suitable enzyme cleavable groups, preferred groups include peptide groups and carbamate bonds. Suitable peptide groups may comprise, for example, 1-5, 1-10, 1-15, 1-20, 1-25, 1-30, 1-35, 1-40, 2-5, 2-10, 2-15, 2-20, 2-25, 2-30, 2-35, or 2-40 amino acid residues. Of course, it should be appreciated that the peptide group may be designed to be specifically cleavable by one or more proteases (e.g., MMP proteases or cathepsin B, or pyrophosphatase). Alternatively, further suitable cleavable groups will have redox sensitivity (disulfide) or light sensitivity.

As already noted earlier, the linker portion in preferred aspects will not only provide a function for cleaving the chelator portion from the linker portion, but also will provide a protein binding group for binding the coupling moiety to a targeting or carrier protein. As will be readily appreciated there are a wide variety of chemistries available for coupling the linker portion to a carrier or other targeting protein, and suitable coupling manners may be chemical (e.g., via lysine-amide coupling, cysteine-disulfide or maleimide coupling), enzymatic (e.g., via transpeptidation, N-glycan engineering, etc), or non-covalent (e.g., via biotin/avidin, etc.). FIG. 2 shows a table of exemplary protein binding groups.

Therefore, suitable protein binding groups include a maleimide group, a haloacetamide group, a haloacetate group, a pyridyldithio group, an N-hydroxysuccinimide ester group, and an isothiocyanate group. In certain preferred embodiments, the protein binding group is a maleimide group. Suitable protein binding groups also include a disulfide group, a vinylcarbonyl group, an aziridine group or an acetylene group (a disulfide group may be activated by a thionitrobenzoic acid (e.g. 5'-thio-2-nitrobenzoie acid) as an exchangeable group). Furthermore, it is noted that a maleimide, pyridyldithio, or N-liydroxysuceinimide ester group can, where appropriate, be substituted by an alkyl group or other more water-soluble groups. In general, a protein binding group will have protein binding properties in a physiological environment, for example, to one or more amino acids on the surface of the protein. The maleimide group, the haloacetamide group, the haloacetate group, the pyridyldithio group, the disulfide group, the vinylcarbonyl group, the aziridine group, and/or the acetylene group will preferably react with thiol (—SH) groups of cysteines, while the N-hydroxysuccinimide ester group and/or the isothiocyanate group preferably will react with an amino group (—NH) of lysine on the surface of a protein.

Viewed from a different perspective, it is therefore preferred that the radionuclide is coupled directly or indirectly with the targeting or carrier molecule via one or more linkers that can be preferentially cleaved in the target environment or at the target molecule so that the drug can be active only at the desired location and/or desired time. Thus, for alpha (beta) emitters, it is preferred that the emitter is only delivered to the tumor microenvironment, or at the target cell (e.g., tumor cell, immune competent cell, etc.). As noted before, any suitable linkers that can be preferentially cleaved in the tumor microenvironment and/or upon activation of immune system are contemplated.

One preferred linker includes a linker that is cleavable in a mild acidic environment (e.g., at a pH between 3-6, at a pH between 4-6, at a pH between 4.5-5.5, etc.), yet stable in a neutral pH. For example, preferred acid-labile linkers include a thimaleamic acid linker and an acid-cleavable hydrazine linker (e.g., hydrazine linker, (6-maleimidocaproyl) hydrazine-type linker, etc.). It is contemplated that any functional moieties including a drug molecule (either an anti-cancer drug or a marker molecule) coupled to the masking molecule via an acid-labile linker can be released in the mildly acidic tumor microenvironment, such that the functional moieties can selectively and specifically target the tumor microenvironment. Further suitable examples for acid labile linkers include those described in U.S. Pat. Nos. 5,306,809, 4,618,492, 7,902,144, 8,846,602, US Pat. Pub. No. 2016/0089388, and Int. Pat. Pub. No. WO2014/093815, which are incorporated by references herein.

Another preferred type of linker includes a photo-cleavable linker that can be cleaved upon exposure to UV light, visible light, or infrared light. For example, some preferred photo-cleavable linkers include a dimethoxynitrobenzyl (DMNB) group-containing photocleavable linker that is cleaved upon exposure to UV wavelength, a 8-bromo-7-hydroxyquinoline-containing photocleavable linker (e.g., 8-Bromo-2-methylquinolin-7-yl benzenesulfonate, 8-Bromo-2-formylquinolin-7-yl benzenesulfonate) that is cleaved upon exposure to UV wavelength, a 6-bromo-7-hydroxycoumarin-4-ylmethyl-containing photocleavable linker that is cleaved upon exposure to infrared wavelength, a two-photon-cleavable 7-diethylaminocoumarin-based photocleavable linker, an aminoacrylate-based photocleavable linker that can be cleaved upon exposure to visible light (e.g., 400 and 700 nm), or a C4'-N-dialkylamine heptamethine cyanine-based photocleavable linker that can be cleaved upon exposure to near infrared (e.g., 690 nm). It is contemplated that any functional moieties including a drug molecule (either an anti-cancer drug or a marker molecule) coupled to the masking molecule via a photocleavable linker can selectively and specifically be released in the tumor microenvironment when the appropriate light stimulus is focally provided to the tumor microenvironment.

Still another preferred type of linker includes an enzyme-cleavable linker. While any enzymes that may be specifically active in the extracellular tumor microenvironment are contemplated, the preferred enzyme-cleavable linker may include a peptide fragment that is cleavable by granzyme (e.g., fragment including VDDD consensus sequence for human granzyme B, etc.), which is released by NK cells or NKT cells upon activation. Thus, it is contemplated that any functional moieties including a drug molecule (either an anti-cancer drug or a marker molecule) coupled to the masking molecule via the granzyme-cleavable linker can be selectively and specifically be released when the NK cells or NKT cells are activated in the tumor microenvironment (e.g., upon recognition of tumor antigens). Any suitable enzyme-cleavable linkers are contemplated, and exemplary linkers are described in, for example, U.S. Pat. No. 7,902,144, US Pat. Pub. No. 2016/0089388, and Int. Pat. Pub. No. WO2014/093815, which are incorporated by references herein.

Alternatively, the inventors also contemplate an enzyme released by the tumor cell and a linker that can be cleaved by such enzyme can be used as well. For example, the enzyme-cleavable linker may include a peptide fragment that is cleavable by matrix metalloprotease (MMP) (e.g., MMP-2, MMP-9, cleaving P-X-X-Hy motif). In such example, it is contemplated that a drug molecule (either an anti-cancer drug or a marker molecule) coupled to the targeting molecule via MMP-cleavable linker can be selectively and specifically released in the tumor microenvironment where the MMP expression by the tumor cell is increased.

Among other suitable carrier or targeting proteins, particularly preferred proteins include albumin, lactoferrin, and immunoglobulins. Advantageously, such proteins need not be isolated from an individual prior to coupling, but in at least some instances, the protein binding group will have sufficient reactivity to covalently couple the coupling moiety to the carrier or targeting proteins in vivo. However, in further preferred aspects, and particularly where the carrier or targeting protein has affinity to a patient and/or tumor specific antigen (e.g., antibody or antigen-binding fragment thereof, or scFv, or other high-affinity ($K_D$<$10^{-7}$M) binder), the carrier or targeting protein can also be coupled to the coupling moiety in vitro. Therefore, contemplated compounds and compositions will typically include a radioisotope that is bound to a coupling moiety, wherein the coupling moiety has a chelating portion that chelates the radioisotope and a binding portion that allows covalent coupling to a polypeptide. Moreover such compounds and compositions may be further bound to a protein, and particularly a carrier protein (e.g., albumin, immune globulin, lactoferrin, etc.) or an antibody or antigen-binding fragment thereof (e.g., full length IgG, scFv, etc.).

Consequently, the inventor also contemplates pharmaceutical compositions and kits that include the compounds and compositions presented herein, typically in combination with one or more diluents, fillers, salts, buffers, stabilizers, solubilizers, and other materials well known in the art.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions based on its pKa and other properties. Buffers are well known in the art. Accordingly, the buffers described herein are not intended to constitute an exhaustive list, but are provided merely as exemplary buffers that may be used in the formulations or compositions of the invention. In certain embodiments, a buffer includes, but is not limited to Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino) ethanesulfonic acid (MES), maleate, bis-tris, phosphate, carbonate, and any pharmaceutically acceptable salts and/or combinations thereof.

In some embodiments, a pH-adjusting agent may be included in the compositions. Modifying the pH of a composition may have beneficial effects on, for example, the stability or solubility of a therapeutically effective substance, or may be useful in making a composition suitable for parenteral administration. Various pH-adjusting agents are well known in the art. Accordingly, the pH-adjusting agents described herein are not intended to constitute an exhaustive list, but are provided merely as exemplary pH-adjusting agents that may be used in the compositions. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

Some therapeutic agents that are target-specific and effective in treating a tumor often cannot be used clinically due to their high toxicities to non-tumor tissues. The inventors now discovered that radioisotopes (and especially alpha emitters) can be more effectively and safely administered to the cancer patient using a release mechanism that favors a microenvironment of a tumor a releasing mechanism that can be controlled by a medical provider.

Contemplated compounds and compositions can be used to treat solid tumors as well as hematological malignancies. It is believed that the compounds will act by covalently binding to albumin (or other carrier or targeting protein) where the free thiol of cysteine-34 of albumin binds the compound via a Michael addition. Contemplated compound-albumin conjugates will thus circulate in the bloodstream until reaching a tumor, where the lower pH in the tumor microenvironment (or other cleavage condition) results in cleavage of the acid labile bond, thereby releasing the chelator. Moreover, as tumor tissue typically has a high nutrient demand, and as many nutrients are coupled to albumin, albumin uptake into the tumor cells (across plasma membrane and across microvasculature) is enhanced, and with that preferential uptake of the therapeutic alpha emitter. Likewise, separation of the emitter from the carrier protein may be achieved by enzymatic cleavage by enzymes preferentially expressed in a tumor, or where a treatment site is accessible by a light source, via photolytic cleavage.

In some embodiments, contemplated compounds or compositions are administered via systemic injection including subcutaneous, subdermal injection, or intravenous injection. In other embodiments, where the systemic injection may not be efficient (e.g., for brain tumors, etc.) or more localized treatment is desired, it is contemplated that the contemplated compounds or compositions are administered via intratumoral injection.

As used herein, the term "administering" contemplated compounds or compositions refers to both direct and indirect administration of the compound or composition (formulation). Direct administration of the formulation is typically performed by a health care professional (e.g., physician, nurse, etc.), and indirect administration includes a step of providing or making available the formulation to the health care professional for direct administration (e.g., via injection, infusion, oral delivery, topical delivery, etc.). In some embodiments, the drug complex formulation is administered via systemic injection including subcutaneous, subdermal injection, or intravenous injection. In other embodiments, where the systemic injection may not be efficient (e.g., for brain tumors, etc.), it is contemplated that the formulation is administered via intratumoral injection.

With respect to dose of contemplated compounds or compositions, it is contemplated that the dose may vary depending on the status of disease, symptoms, tumor type, size, location, patient's health status (e.g., including age, gender, etc.), specific activity of the composition, and any other relevant conditions. While it may vary, the dose and schedule may be selected and regulated so that contemplated compounds or compositions do not provide any significant toxic effect to the host normal cells, yet sufficient to be effective to induce an cytotoxic effect and/or immune-modulatory effect against the tumor and/or the tumor microenvironment such that size of the tumor is decreased (e.g., at least 5%, at least 10%, at least 20%, etc.), the number of tumor cells is decreased, the phenotype of the tumor is changed (e.g., shape, change in gene expression, change in protein expression, change in post-translational modification of a protein, etc.), activity of M2-polarized macrophage is decreased, and/or the accumulation of MDSC and/or Tregs is prevented (or stopped, decreased, etc.).

In some embodiments, especially where a photo-labile linker is employed, contemplated radionuclides can be released upon an appropriate photo stimulus. Suitable wavelength, light source, timing and frequency of the photo stimulus may vary depending on the type of photo-labile linker and the type of carried anti-cancer drug. For example, where the suitable wavelength is infrared or near infrared light, which can penetrate relatively, deep into the tissue, or the tumor is located close to the skin (e.g., skin cancer, etc.), the light can be applied to the tumor from the outside of the patient's body (e.g., near the skin, etc.). In another example, where the suitable wavelength is a UV or visible light, the light can be applied locally inside of the patient's body (e.g., near the tumor) via micro light emitter inserted near the tumor or embedded near the tumor. Optionally, the light stimuli can be provided in a predetermined frequency (e.g., 1 Hz, 0.5 Hz, 0.1 Hz, or every 10 min, every 30 min, every 1 hour, every 3 hours, etc.) and duration (e.g., for 6 hours total, 3 hours total, 1 hour total, etc.).

The inventors further contemplate that the compositions and methods described above can be used to determining active release of the radionuclide (typically together with a chelator or other group to which the isotope is bound) in the tumor microenvironment, preferably/with a marker that may be released in the same condition with the radionuclide is released. Without wishing to be bound to any specific theory, it is contemplated that at least a portion of the released marker molecule can be released into the peripheral blood stream as a cell free nucleic acid, preferably cell-free DNA. The presence of the marker molecule in the patient's blood can be determined and the quantity of the marker molecule should be readily quantified using the real-time PCR or any other available DNA quantification methods. Thus, detection of the marker molecule in the patient's blood stream can indicate the release of the radionuclide in the tumor microenvironment, and can even further determine the amount of radionuclide released as it is expected to be proportional to the amount of the marker molecule.

In some embodiments, the radionuclide complex can be coupled to two different marker molecules (e.g., two different DNA fragments having distinct sequences and/or length) by two different types of linkers such that two different markers can be released at different time points and/or different environmental conditions. For example, the radionuclide complex may be coupled to a marker molecule A via a granzyme-cleavable linker and a marker molecule B via an acid-labile linker. Once the radionuclide complex is administered to the patient and enters the tumor microenvironment, it is likely that the marker molecule A can be released under the acidic condition of the tumor microenvironment. Then, marker molecule B can be released via granzyme that may be present upon the activation of immune competent cell in the tumor microenvironment. Thus, in such scenario, the patient's blood sample can be periodically used to detect the presence and quantify marker molecule A and/or B. The absolute quantities and/or ratio of the marker molecule A and/or B may reflect the condition of the tumor microenvironment.

The terms "patient" and "individual" are used interchangeably and refer to either a human or a non-human animal. These terms include mammals such as humans, primates, livestock animals (e.g., bovines, porcines), companion animals (e.g., canines, felines) and rodents (e.g., mice and rats).

The term "pharmaceutically acceptable" means a nontoxic material that does not interfere with the effectiveness of the biological activity of the active ingredient(s). The characteristics of the carrier will depend on the route of administration. The term "pharmaceutically acceptable carrier" refers to a non-toxic carrier that may be administered to a patient, together with a therapeutically effective substance of this invention, and which does not destroy the pharmacological activity of the cytotoxic agent. The term "excipient" refers to an additive in a formulation or composition that is not a pharmaceutically active ingredient.

The term "pharmaceutically effective amount" or "therapeutically effective amount" refers to an amount effective to treat brain cancer in a patient, e.g., effecting a beneficial and/or desirable alteration in the general health of a patient suffering from a disease (e.g., cancer). The skilled worker will recognize that treating brain cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. A "pharmaceutically effective amount" or "therapeutically effective amount" also refers to the amount required to improve the clinical symptoms of a patient. The therapeutic methods or methods of treating brain cancer described herein are not to be interpreted or otherwise limited to "curing" brain cancer.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

The invention claimed is:

1. A synthetic alpha-emitter-conjugated compound, consisting essentially of:

an alpha-emitter coupled to a coupling moiety that comprises a linker portion and a chelator portion;

wherein the linker portion has a protein binding group and wherein the chelator portion chelates the alpha-emitter;

wherein the coupling moiety comprises an acid labile hydrazone moiety that is cleavable in an acidic tumor microenvironment;

wherein the coupling moiety is represented by the following Formula 1:

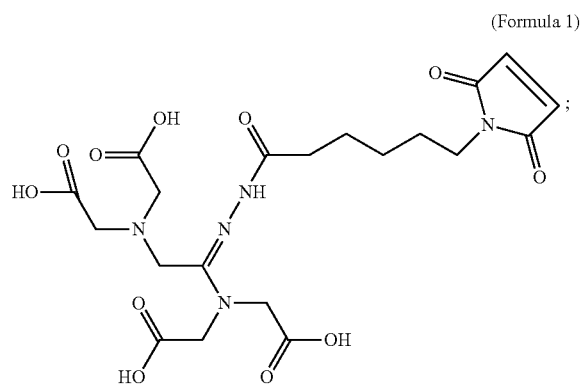 [SMILES: O=C(O)CN(CC(=O)O)CC(=NNC(=O)CCCCCN1C(=O)C=CC1=O)N(CC(=O)O)CC(=O)O]

(Formula 1)

and optionally a protein coupled to the protein binding group.

2. The compound of claim 1, wherein the alpha-emitter is $^{225}$Ac, $^{211}$At, $^{212}$Pb and $^{213}$Bi, or $^{223}$Ra.

3. The compound of claim 1, comprising the protein coupled to the protein binding group.

4. The compound of claim 3, wherein the protein is an antibody or a fragment thereof.

5. The compound of claim 3, wherein the protein is an albumin.

6. A method of delivering an alpha-emitter to a tumor, comprising:

administering an alpha-emitter coupled to a coupling moiety that comprises a linker portion and a chelator portion;

wherein the linker portion has a protein binding group and wherein the chelator portion chelates the alpha-emitter;

wherein the coupling moiety comprises an acid labile hydrazone moiety that is cleavable in an acidic tumor microenvironment; and wherein the coupling moiety is represented by the following Formula 1:
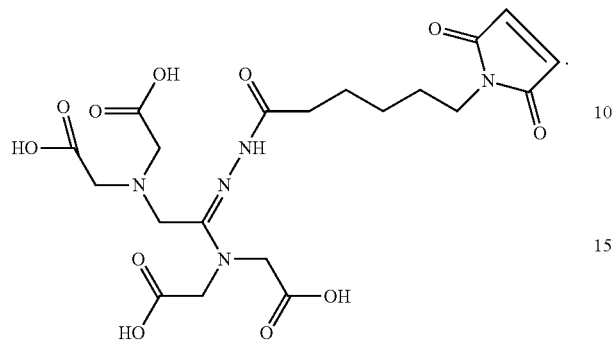
(Formula 1)
7. The method of claim 6, wherein the alpha-emitter is $^{225}$Ac, $^{211}$At, $^{212}$Pb and $^{213}$Bi, or $^{223}$Ra.
* * * * *